United States Patent [19]

Goldhaber

[11] 4,140,633

[45] Feb. 20, 1979

[54] METHOD AND APPARATUS FOR DETERMINING ULTRAFILTRATION DURING DIALYSIS

[75] Inventor: Richard P. Goldhaber, Libertyville, Ill.

[73] Assignee: Baxter Travenol Laboratories, Inc., Deerfield, Ill.

[21] Appl. No.: 787,983

[22] Filed: Apr. 15, 1977

[51] Int. Cl.$^2$ ............................................. B01D 31/00
[52] U.S. Cl. ................................. 210/95; 210/321 B
[58] Field of Search ............ 210/22, 96 M, 87, 321 B, 210/95; 128/214 R; 23/258.5 M

[56] References Cited

U.S. PATENT DOCUMENTS

| | | | |
|---|---|---|---|
| 3,844,940 | 10/1974 | Kopf et al. | 210/96 M X |
| 3,909,377 | 9/1975 | Bizot et al. | 210/22 D X |
| 3,946,731 | 3/1976 | Lichtenstein | 210/87 X |
| 3,990,973 | 11/1976 | Boag et al. | 210/87 |

Primary Examiner—Frank A. Spear, Jr.
Attorney, Agent, or Firm—Garrettson Ellis; Paul C. Flattery

[57] ABSTRACT

The ultrafiltration provided by an operating dialyzer is measured by sealing a portion of the dialysis solution flow path, including the dialysis unit, to prevent solution flow into or out of the portion, while effecting flow of the liquid to be dialyzed through a second flow path in the dialysis unit. Simultaneously, the dialysis solution flow path is in communication with a solution receptacle, at least part of which is vertically elevated over the dialysis unit. Accordingly, dialysis solution flows into the receptacle over a period of time under these conditions in a manner corresponding to the ultrafiltration of the dialysis system.

16 Claims, 6 Drawing Figures

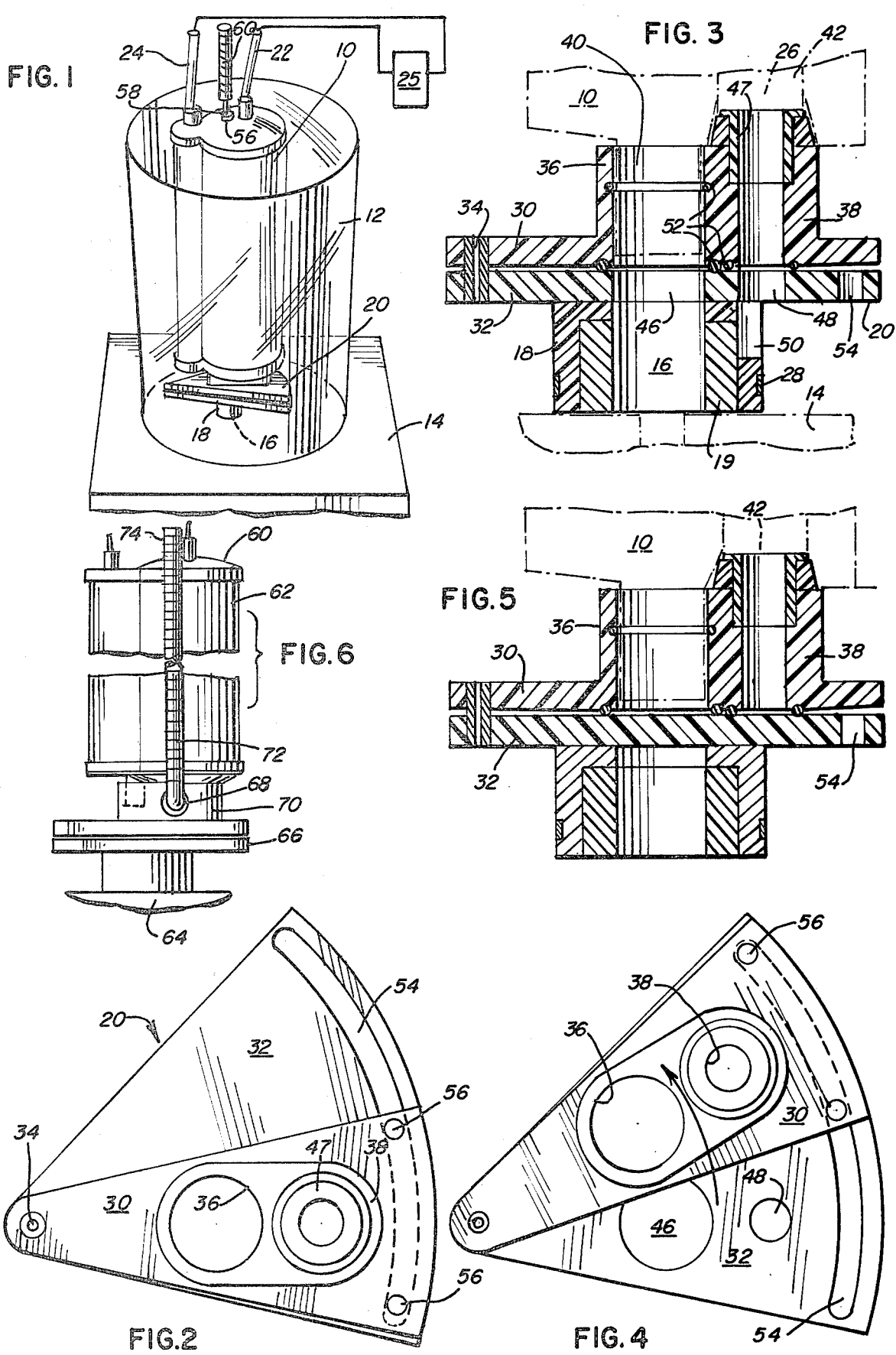

METHOD AND APPARATUS FOR DETERMINING ULTRAFILTRATION DURING DIALYSIS

BACKGROUND OF THE INVENTION

In dialysis, and particularly in hemodialysis, the rate of ultrafiltration (water removed from the solution to be dialyzed) is a critical matter, and one which particularly must be carefully controlled during a blood dialysis procedure with a patient.

Currently, ultrafiltration can be calculated from the mean dialyzer pressure differential between the blood flow path and the dialysis solution flow path by taking the arithmetic mean of the overall dialyzer pressure. This however requires the measurement of pressure both at the dialysis solution inlet and the outlet, and additional equipment to accomplish it. Also, it is not necessarily an accurate way to measure ultrafiltration, particularly in the case where for any of various reasons the integrated sum total area of the dialyzer pressure differential is not equal to arithmetic mean pressure differential.

Another technique for measuring ultrafiltration is to seal off the dialyzer and to shut off the blood pump, to get an integrated pressure as a direct read-out of pressure in the bubble trap of conventional dialysis blood line systems. It is, however, most undesirable to stop the blood pump during dialysis procedures.

The technique for measuring ultrafiltration utilized in this invention is a direct measurement of ultrafiltration over a limited period of time, without stopping of the flow of blood or other liquid to be dialyzed. Accordingly, from this data the overall ultrafiltration over a larger period of time can be extrapolated, with the results being reconfirmed from time to time by repeated testing of the ultrafiltration rate over a short period of time. The method of this invention may therefore be accomplished without complete halting of the dialysis procedure, and, with the apparatus of this invention, the testing for direct measurement of ultrafiltration may be conveniently performed at any desired time or times during the dialysis procedure.

DESCRIPTION OF THE INVENTION

In accordance with this invention, ultrafiltration in a dialysis system is measured during operation. The system comprises a dialysis unit positioned in a dialysis solution flow path, the dialysis unit also being positioned in a second flow path for liquid to be dialyzed. The dialysis solution flow path and the second flow path are separated in the dialysis unit in a usual manner by a semi-permeable membrane. The dialysis solution flow path is also in communication, adjacent the dialysis unit, with a solution receptacle in a vertically elevated position.

Accordingly, to accomplish the method of this invention, a portion of dialysis solution flow path, including the dialysis unit, is sealed to prevent solution flow into or out of the dialysis solution flow path portion except through the membrane. Simultaneously, the flow of liquid may continue through the second flow path. As a result of this, any ultrafiltration between the second flow path to the dialysis solution flow path which takes place during the period of time that these conditions are maintained results in a flow of solution between the solution receptacle and the first flow path in a manner corresponding to the ultrafiltration rate of the dialysis system.

In particular, with the embodiment described in FIG. 1 of the drawings described below, if during five minutes of maintenance of the conditions described above, the liquid level in the receptacle increases by 100 cc., it can be known that the ultrafiltration rate of the dialysis system at that time is 100 cc. per five minutes. If the dialysis procedure had continued for an hour, it can then be known that 1200 cc. of ultrafiltration must have taken place.

Preferably, the portion of the dialysis solution flow path which is sealed off consists essentially of only the flow path within the dialysis unit, to reduce the volume of the sealed-off flow path as much as possible.

The invention of this application may be utilized in conjunction with any desired dialysis system and dialysis units including coil-type dialyzers, flat plate dialyzers, or fiber dialyzers as desired. Also, the invention can be used with reverse osmosis devices or ultrafiltration devices using a semi-permeable membrane, which devices are considered also to fall within the category of dialysis systems for purposes of this invention.

While the ultrafiltration in the usual dialysis arrangement is expected to flow from the second flow path to the first flow path, this invention can be utilized, as in a reverse osmosis device or an ultrafiltrator, where the ultrafiltration is from the first to the second flow path. In this case, the ultrafiltration can be measured by prefilling the receptacle with liquid, and observing the drop in liquid level over time under the conditions described in this invention.

As specifically disclosed, the means for sealing a portion of the dialysis solution flow path comprises a valve arrangement for providing an intermittently open and sealed portion of the dialysis solution flow path. The valve or sealing means is preferably adapted to seal or isolate a portion of the dialysis solution flow path which consists essentially of only the flow path within the dialysis unit, to minimize the volume of solution in the isolated area for improved accuracy in the measurement of ultrafiltration.

The sealing means may comprise a first sliding member and a second sliding member positioned against each other in sealing relation. Aperture means are defined through the first and second sliding members to permit the dialysis solution flow path to pass therethrough. Connection means are carried by the first sliding member for sealingly connecting the apertures to corresponding apertures in the dialysis unit, to provide a sealed connection of the dialysis solution flow path through the sliding members and the dialysis unit.

Movable retention means connect the sliding members so that their respective apertures may be positioned in registry one with another in a first sliding position, to provide an open dialysis solution flow path through the sliding members in the dialysis unit. Also, the sliding members may be moved into a second sliding position, whereby their respective apertures are not in registry one with another, to seal the dialysis solution flow path and to isolate the portion of the dialysis solution flow path within the dialysis unit, for ultrafiltration measurement in accordance with this invention.

The exterior aperture, to which access to the dialysis solution flow path is obtained for measurement of the ultrafiltration, may be sealed with a conventional, needle-pierceable injection site, and may be positioned at the top of the dialysis unit for access by a syringe member. Alternatively the exterior aperture may be positioned adjacent the first and second sliding members, to permit the use of this invention with conventional, disposable dialysis units, the aperture being in communication with a vertically extending tubular conduit leading from the aperture to a position above the normal location of the dialysis unit, so as to retain the volume of ultrafiltration liquid. If desired, the tubular member may define graduations on it for measurement of liquid within it.

In the drawings,

FIG. 1 is a perspective view of a portion of a dialysis system utilizing the invention of this application.

FIG. 2 is a plan view of the sealing means utilized in this invention for providing an alternately open and sealed portion of the dialysis solution flow path, shown in the first open position.

FIG. 3 is a sectional view taken along the axis of the upper sliding member of FIG. 2.

FIG. 4 is a plan view similar to the structure of FIG. 2, but showing the upper sliding member in its second, sealing position.

FIG. 5 is a sectional view of the structure of FIG. 5, taken along the same axis of the upper sliding member in its second position.

FIG. 6 is an elevational view of an alternative embodiment of the dialysis solution delivery system of this invention.

Referring to FIG. 1, a dialysis solution delivery system is shown comprising a coil-type membrane dialyzer 10 of generally conventional structure, except as otherwise described herein. Dialysis unit 10 is enclosed in a canister 12 which may be open at the top. Dialysis solution console 14, of conventional structure, is adapted to deliver dialysis solution through a central delivery aperture 16 which, in turn, is enclosed by a sleeve 18.

Above sleeve 18 is positioned the sealing means 20 for providing an alternatively open and sealed dialysis solution flow path, as more particularly described herein.

Blood inlet 22 is provided in the coil dialyzer 10, communicating with one end of the flattened membraneous tubing within the dialyzer. Blood outlet 24 is also provided, with the flow path between inlet 22 and outlet 24 constituting the second flow path within the dialyzer. Conventional blood pump and circuit means 25 is schematically represented, for circulating the blood, as well as withdrawing it from and returning it to the patient.

The first flow path for dialysis solution passes through dialysis solution delivery port 16, through the valving means 20 into the dialyzer unit 10, then passing through outlet 26 into the canister for recycling, or partial or complete removal from the system as desired by conventional means.

The specifically-shown embodiment of a dialysis unit is a CD ™ brand coil dialyzer manufactured by the Artificial Organs division of Travenol Laboratories, Inc., although other dialyzer units and membrane diffusion devices may be utilized in this invention.

FIGS. 2 through 5 show the valving unit 20 in greater particularity. Sleeve 18, as shown in FIG. 3, may be carried by sleeve 19, which is attached to and projects from the dialysis delivery system console 14. A tightening band 28, of conventional construction, may be utilized to firmly hold the two sleeves 18, 19 together in sealing relationship.

Sleeve 18 carries upper and lower sliding plates 30, 32 which are hingedly connected together by a hinge member 34.

Upper sliding plate 30 carries a double-sleeve member 36, 38 for sealing connection with the dialysis solution inlet 40 and outlet 42 of the dialysis unit 10. In the specific embodiment shown, a dialysis solution inlet 40 of unit 10 is a projecting member which can be received by sleeve 36, while outlet 42 of unit 10 is sealingly engaged in a silicone rubber sealing ring 44, which is held against sleeve 38 by retainer sleeve 47.

Sleeves 36 and 38 of the upper sliding member 30 are in open communication with lower sliding member 32.

In turn, lower sliding member 32 defines a pair of apertures 46, 48 which are in communication, in a first sliding position, with sleeves 36, 38 as shown in FIGS. 2 and 3. Accordingly, dialysis solution passing from the delivery system 14 through aperture 16 passes through aperture 46 and sleeve 36 to inlet 40 of the dialyzer. From there it passes in conventional manner through the dialyzer to outlet 42, passing then in sealed manner through retainer sleeve 47, sleeve 38, and aperture 48 of the lower sliding member, and into the open space of canister 12 for removal or recirculation as desired. Cutaway portion 50 of sleeve 18 facilitates, if necessary, the outflow of dialysis solution through aperture 48.

Sealing rings 52 are provided as shown in the drawings at various places to provide a liquid-tight seal between the various members.

As shown in FIG. 2, lower sliding member 32 defines an arcuate slot 54 which carries sliding retaining pins 56, which are carried in turn by upper sliding member 30.

Upper sliding member 30 carries dialyzer 10 during the dialysis operation. When sliding member 30 is moved, dialysis unit 10 moves with it, blood lines 22, 24 being flexible to accomodate this motion.

When, during the dialysis procedure, it is desired to directly measure the rate of ultrafiltration for a brief period of time, upper sliding member 30, and the dialysis unit it carries, is pivoted from the first position shown in FIGS. 2 and 3 to the second position, relative to the lower sliding member 32, as shown in FIGS. 4 and 5. Pins 56 move in groove 54 as the upper sliding member pivots about member 34. Prior to moving sliding member 30 from the first to second position, the dialysis solution pump in console 14 is shut off. In the second position, sleeves 36, 38 bear against a solid, port-free portion of lower sliding member 32, so that the dialysis solution flow path in dialyzer 10 is sealed at both ends, i.e. inlet 40 and outlet 42.

In the meanwhile, blood pump means 25 may be allowed to continue to operate, to continue the dialysis and ultrafiltration process against the dialysis solution now trapped in dialyzer unit 10.

In an upper portion of dialysis unit 10, a latex injection site 56, or other sealed aperture means, may be positioned, communicating with the dialysis solution flow path at a position safely spaced from the coils of membrane, so that the insertion of a needle will not damage the membrane coils. Injection site 56 may be fabricated in a manner similar to the current injection site utilized on the dialysis solution blood sets which are currently sold by Travenol Laboratories, Inc. for blood dialysis, if desired.

As shown in FIG. 1, a needle 58 which is connected to a vented, graduated burette receptacle 60 is positioned to penetrate injection site 56, to provide a receptacle which is in communication with the dialysis solution flow path within dialysis unit 10, and positioned vertically above the dialysis unit. Accordingly, when the dialysis solution flow path of unit 10 is isolated by means of the configuration of FIGS. 4 and 5, and ultrafiltration continues, liquid will be forced upwardly from the dialysis solution flow path through needle 58 into receptacle 60 at a rate which is dependent upon the amount of ultrafiltration taking place during the dialysis process. Accordingly, the dialysis solution flow path in unit 10 is isolated for a measured period of time, and the amount of liquid collected in receptacle 60 is noted. Thereafter, sliding member 30 is moved back again from the second to the first position as shown in FIG. 2, reopening the flow of dialysis solution through dialysis unit 10. The dialysis solution pumping console 14 is reactivated to continue the dialysis process.

From this operation, the total amount of ultrafiltration which has taken place over the entire dialysis procedure can be calculated by extrapolation, knowing the time that sliding member 30 was in its second position, and the amount of dialysis solution collected in receptacle 60 during that time.

FIG. 6 represents a second embodiment for utilizing the same procedure. Dialysis unit 60 is positioned once again in a canister 62, and connected to a dialysis solution console 64 through a valving means 66, which is similar in design to the previous embodiment except as otherwise indicated. In this embodiment, the dialysis unit 60 carries no injection site similar to site 56. Instead, access is obtained to the dialysis solution flow path by an aperture 68 in a sleeve 70, which generally corresponds to sleeve 36 of the embodiment of FIGS. 1 through 5, with the exception that it may desirably be somewhat taller in order to make room for aperture 68.

A vertically mounted burette member 72 is positioned in sealing communication with aperture 68, and carries a portion 74 which extends vertically above dialyzer member 60.

During normal operation, there will be a liquid level in burette member 72 which is about as high as the dialysis liquid can rise in dialysis unit 60, adjusted for any pressure differential sensed by burette member 72. Upon closing of valve member 66 in a manner similar to the previous embodiment, additional liquid volume in the sealed dialysis solution flow path through ultrafiltration will result in an increase in the liquid level in burette member 72, which can be measured over time as in the previous embodiment.

The above has been offered for illustrative purposes only, and is not for the purpose of limiting the invention of this application, which is as defined in the claims below.

That which is claimed is:

1. In a system for delivery of dialysis solution to a dialysis unit which comprises means for delivering dialysis solution in first flow path means through the dialysis unit, and means for intermittently sealing the first flow path means, said intermittent sealing means comprising a first sliding member and a second sliding member positioned against each other in sealing relation; first and second aperture means defined through said first and second sliding members to define said first flow path passing therethrough; connection means carried by said first sliding member for sealingly connecting said apertures to corresponding apertures in a dialysis unit, to provide a connection of said first flow path means through the sliding members and said dialysis unit in sealing manner, and movable retention means connecting said sliding members, whereby their respective apertures may be positioned in registry one with another in a first sliding position, to provide an open first flow path through said sliding members and dialysis unit, and said sliding members may be moved into a second sliding position whereby their respective apertures are not in registry one with another, to seal said flow path and to isolate the portion of said first flow path which is within the dialysis unit; and exterior aperture means, positioned to provide communication between the first flow path and the exterior of the apparatus, and adapted for connection with a vertically elevated receptacle, whereby in said second sliding position any ultrafiltration into said first flow path within said dialyzer results in a flow of solution through said exterior aperture into said receptacle, when a solution receptacle is in communication with the first flow path through said aperture.

2. The dialysis system of claim 1 in which said first and second sliding members are pivotally attached one to another, and define means for sealing the interface between said first and second sliding members, about their respective apertures, when positioned in the first position.

3. In a dialysis system which comprises a dialysis unit positioned in dialysis solution flow path means, said dialysis unit also being positioned in second flow path means for a liquid to be dialyzed, the dialysis solution flow path means and the second flow path means being separated in said dialysis unit by semi-permeable membrane means; exterior aperture means positioned to communicate with the dialysis solution flow path means, and adapted for connection with a vertically elevated solution receptacle, normally unfilled with liquid, for communication between said receptacle and the dialysis solution flow path means, sealing means for providing an alternatively open and sealed portion of said dialysis solution flow path means, including said dialysis unit and exterior aperture means, to prevent solution flow into or out of said portion in sealed mode except through said membrane means; said sealing means comprising a first sliding member and a second sliding member positioned against each other in sealing relation; first and second aperture means defined in said first and second sliding members to permit said dialysis solution flow path to pass therethrough; connection means carried by said first sliding member for sealingly connecting said apertures to corresponding apertures in said dialysis unit to provide connection of said dialysis solution flow path through said sliding members and said dialysis unit in sealing manner; and retention means connecting said sliding members, whereby their respective apertures are positioned in registry, one with another in a first sliding position, to provide an open dialysis solution flow path through said sliding members and dialysis unit, and permitting said sliding members to be moved into a second sliding position whereby their respective apertures are not in registry with one with another, to seal said dialysis solution flow path and to isolate the portion of said dialysis solution flow path which is within the dialysis unit.

4. The dialysis system of claim 3 in which said exterior aperture means is defined by a needle-pierceable injection site, said receptacle comprising a needle penetrating said injection site and in flow communication with a tubular, vented, graduated member for receiving and measuring solution from said dialysis solution flow path.

5. The dialysis system of claim 4 in which said exterior aperture means is positioned on the top of said dialysis unit.

6. The dialysis system of claim 3, including pump means for causing liquid to pass through said dialysis solution flow path, when the flow path is open, and pump means to cause liquid to pass through said second flow path, whereby any ultrafiltration between said second flow path means to the dialysis solution flow path means, when liquid is flowing through said second flow path means, and said dialysis solution flow path portion is sealed, results in a flow of solution between said exterior aperture and said receptacle when a solution receptacle is in communication with the dialysis solution flow path means through said aperture means.

7. The dialysis system of claim 6, in which said exterior aperture means positioned to communicate with a dialysis solution flow path is positioned adjacent said sliding members, said apparatus further including a vertically extending tubular conduit leading from said exterior aperture means to a position above said dialysis unit.

8. The dialysis system of claim 6 in which said dialysis unit is carried by sliding valve means for sealing a portion of the dialysis solution flow path, including said dialysis unit, whereby the sliding valve means can be opened and closed by manipulation of the dialysis unit.

9. The dialysis system of claim 6 in which said sealing means is adapted to seal and isolate a portion of the dialysis solution flow path means which consists essentially of only the flow path within said dialysis unit.

10. The dialysis system of claim 9 which is a hemodialysis system, said second flow path means being adapted for passing blood through said dialysis unit.

11. The dialysis system of claim 6 in which said first and second sliding members are pivotally attached one to another, and define means for sealing the interface between said first and second sliding members, about their respective apertures, when positioned in the first position.

12. The dialysis system of claim 11 in which said second sliding member carries means for connection to a source of dialysis solution in dialysis solution delivery apparatus.

13. The dialysis system of claim 12 in which said means for sealing a portion of said dialysis solution flow path is adapted to seal a portion of the dialysis solution flow path which consists essentially of only the flow paths within the dialysis unit.

14. The dialysis system of claim 13 in which said exterior aperture means, positioned, to communicate with the dialysis solution flow path is defined by a needle-pierceable injection site, said receptacle comprising a needle penetrating said injection site and in flow communication with a tubular, vented, graduated member for receiving and measuring solution from said dialysis solution flow path.

15. The dialysis system of claim 14 in which said exterior aperture means is positioned on the top of said dialysis unit.

16. The dialysis system of claim 15 which is a hemodialysis system, said second flow path means being adapted for passing blood through said dialysis unit.

* * * * *